United States Patent [19]

Sherman

[11] Patent Number: 4,510,065

[45] Date of Patent: Apr. 9, 1985

[54] SOFT CONTACT LENS PRESERVATIVE SYSTEM, PROPHYLACTIC CLEANER AND METHOD

[75] Inventor: Guy J. Sherman, Mandeville, La.

[73] Assignee: Sherman Laboratories, Inc., Abita Springs, La.

[21] Appl. No.: 537,257

[22] Filed: Sep. 28, 1983

Related U.S. Application Data

[63] Continuation-in-part of Ser. No. 384,110, Jun. 1, 1982, abandoned, which is a continuation-in-part of Ser. No. 53,758, Jul. 2, 1979, abandoned.

[51] Int. Cl.$^3$ .................... C11D 3/48; C11D 1/72
[52] U.S. Cl. .................... 252/106; 252/153; 252/173; 252/174.21; 252/174.22; 252/542; 252/545; 252/546; 252/DIG. 14
[58] Field of Search .............. 252/106, 542, 545, 546, 252/153, 173, 174.21, 174.22, DIG. 14; 428/280

[56] References Cited

U.S. PATENT DOCUMENTS

| | | | |
|---|---|---|---|
| 3,329,607 | 7/1967 | Colobert | 252/181 X |
| 3,908,680 | 9/1975 | Krezanoski | 134/27 |
| 3,954,644 | 5/1976 | Krezanoski et al. | 252/106 |
| 4,013,576 | 3/1977 | Loshaek | 252/106 |
| 4,031,209 | 6/1977 | Krezanoski | 424/150 |
| 4,104,187 | 8/1978 | Sibley et al. | 252/106 |
| 4,199,469 | 4/1980 | Walzer | 252/180 |

FOREIGN PATENT DOCUMENTS 2003033  3/1979  United Kingdom .

Primary Examiner—Prince E. Willis
Attorney, Agent, or Firm—Jenner & Block

[57] ABSTRACT

Preservative systems which may be incorporated into aqueous compositions for the daily cleaning of silicone copolymer (gas-permeable) and soft contact lenses are provided. The preservative system includes trimethoprim, a salt of EDTA and an adjuvant bactericide that is either sorbic acid or ascorbic acid. One suitable cleaning composition which incorporates the preservative system includes three types of detergents. The cleaning composition is effective in removing both proteins and lipids from the surfaces of soft contact lenses and aids in preventing deposits from forming and binding to the lenses.

38 Claims, No Drawings

SOFT CONTACT LENS PRESERVATIVE SYSTEM, PROPHYLACTIC CLEANER AND METHOD

RELATED APPLICATION

This application is a continuation-in-part of U.S. patent application Ser. No. 384,110, filed June 1, 1982 which is a continuation-in-part of U.S. patent application Ser. No. 53,758, filed July 2, 1979 both abandoned.

BACKGROUND OF THE INVENTION

Just as there are marked differences in the structure and composition of hard, cellulose-acetate-butyrate (CAB) gas-permeable and silicone copolymer gas-permeable contact lenses and soft contact lenses, there are also marked differences in the maintenance, care and treatment of the various types of hard, CAB, silicone and soft lenses. While patient care and treatment of hard contact or conventional contact lenses is relatively simple and uncomplicated, the proper care and treatment of CAB and silicone copolymer lenses (gas-permeable) and the newer soft and hydrophilic lenses has proved to be more complex, time consuming and costly to the patient.

The primary difference between the conventional hard contact lens and the silicone copolymer lenses and the more complex soft lenses is the hydrophobic nature of the silicone copolymer lenses and marked increase in the polar or water attracting centers of the hydrophilic gel material from which the soft contact lenses are made. It is this property of the hydrophilic gel lens that gives the soft lens its own unique physical properties and clinical behavior. This polar or water attracting center of the gel material is represented in the hydroxyethyl methacrylate bond as a hydroxyl group (—OH) which attracts and holds large amounts of water. It is this high water content held in the expanded matrix of the hydrophilic gel lens which leads to the special difficulties in cleaning and disinfecting or asepticising the soft hydrophilic lens. The hydrophilic nature of soft contact lenses makes the lenses vulnerable to bacterial contamination. While studies have demonstrated that bacteria cannot penetrate the actual intramolecular pores of the hydrophilic lens, except in defective lenses, the bacteria have an affinity for protein and tear deposits on the surfaces of the lens matrix. In particular, the tears and fluids absorbed by the soft lenses serve as excellent bacterial culture media. If defects or nicks occur in the lenses either during manufacture or subsequent patient wear, bacteria may find a haven to grow and be sheltered from superificial lens cleaning and disinfection.

Potentially harmful fungi are also a possible danger to the soft contact lens. Fungi, like bacteria, can thrive in tear secretions, other fluids or deposits and penetrate the lens material directly if enzymatic degradation of the lens material has taken place.

Similarly, any substantial residual proteinaceous or tear secretion deposits or lipid deposits remaining in or on the lens may readily overwhelm and inactivate the most effective germicidal components of a disinfecting system, and may thus serve to act as a growth media for a variety of potentially harmful microorganisms and fungi. Therefore, it is important that prior to storing the soft contact lenses in a disinfecting solution, protein and lipid deposits be removed from the lens surfaces so that the disinfectant properties of the sterilizing solution or method will not be overwhelmed by gross organic or inorganic deposits and pollutants. Therefore, an effective cleaning step or steps is an essential and mandatory part of any effective soft lens treatment and maintenance regimen.

Numerous methods of cleaning soft contact lenses to remove only protein deposits exist. For example, the soft lenses can be rinsed in tap water in an attempt to remove protein deposits. Tap water rinsing is virtually ineffective, removing only from about 1% to about 10% of the accumulated debris on the lens surfaces. Boiling the soft contact lenses in a saline solution is partially effective, removing generally from about 5% to 15% of the debris located on the lens surfaces. Other cleaning methods include the use of hydrogen peroxide and sodiium chloride solutions. Hydrogen peroxide is ineffective since it will actually oxidize and change the color of the lenses. Use of high concentrations of sodium chloride aids in removing some encrustations because of the friction created in rubbing the lenses with a sodium chloride solution. However, this method is harmful to the lenses because scratching of the lens surfaces occurs. Enzymatic cleaners do not remove deposits such as salts, lipids and mucin. In addition, the enzymatic cleaners may also discolor the soft contact lenses. A more detailed discussion of various types of cleaning procedures and compositions is found in the April 1978 issue of Review of Optometry in a series of three articles, one each by: Irving J. Arons; Jerome S. Lieblein, O.D.; and Frederick D. Kleist and Jon C. Thorson, M.D.

Therefore, a need has arisen for an effective conposition to remove protein, lipid and other deposits which tend to remain on gas permeable and soft contact lenses after a wearing period has been completed. A need has also arisen for a gas permeable and soft contact lens cleaner that can be easily rinsed from the lens surfaces after cleaning has been accomplished and that does not contain components which significantly bind to the lens or are otherwise deleterious to the lens material.

Since contact lenses are susceptible to bacteria and fungi, the cleaner should contain a preservative system to insure that the cleaning solution does not become contaminated by such organisms, the use of which could transfer the organisms to the lenses. Compounds such as thimerosal and chlorhexidine, which are known for use in preservative systems for maintaining a solution sterile or essentially sterile have been used. However, these compounds have drawbacks in that they can be concentrated in the lens matrix and cause irritation, excessive burning and red eye, which can prevent the patient from wearing the lenses. With the advent of extended wear lenses, it becomes even more important to avoid such problems, since those lenses can remain in the eye for several weeks.

SUMMARY OF THE INVENTION

This invention relates to novel and effective silicone copolymer (gas permeable) and soft contact lens preservative systems and prophylactic cleaning compositions for removing deposits from the surface of the lenses. More particularly, this invention relates to highly effective silicone copolymer and soft contact lens cleaners for use after each wearing day is completed that remove lipids and proteins from the surfaces of the lenses and a preservative system which avoids hypersensitivity problems associated with preservative systems containing thimerosal or chlorhexidine, for example. The invention is especially suitable for use on CAB, silicone copolymer and soft lenses (such as HEMA contact lenses, for example) including extended wear contact lenses, and reference to soft lenses includes CAB, silicone copolymer and extended wear lenses. The invention is also suitable for use in connection with hard contact lenses.

In another aspect, this invention relates to a soft contact lens cleaning composition that will remove both proteins, lipids and other foreign deposits from the surfaces of the contact lens thereby eliminating interference with wearing comfort which can be caused by such deposits. In addition, the cleaning composition helps maintain clear vision throughout each wearing period. In another aspect, this invention relates to an efficient cleaner for soft contact lenses that is simple to use and can be easily rinsed from the contact lens after the cleaning is completed.

In accordance with the invention, a preservative system is provided that is incorporated in a contact lens cleaning solution. The preservative system is effective for maintaining the solution sterile, preventing bacteria and other organisms from contaminating the solution after its container has been opened and an initial use has been made of a portion of the solution, for example. While intended primarily for use in connection with soft contact lenses, the preservative system may also be used in connection with hard contact lenses.

The preservative system of the invention is safe and effective and is not deleterious to the human eye or ocular tissue. Thus, if a cleaning composition containing the preservative system is not adequately rinsed from the lens, harmful effects and/or discomfort does not occur. Further, the preservative system does not discolor soft contact lenses and is not otherwise deleterious to soft lenses. Accordingly, the shortcomings of preservative systems containing compounds such as thimerosal or chlorhexidine, for example, are avoided.

The preservative system of the invention for use in a contact lens cleaning composition includes trimethoprim and adjuvant bactericides, present together in effective amounts for maintaining sterility of the cleaning composition. The adjuvant bactericides include ethylenediaminetetraacetic acid (EDTA) or a water soluble salt thereof and sorbic acid. Ascorbic acid, or a salt thereof, may be utilized in place of or in addition to sorbic acid. Usually, an effective amount of trimethoprim is from about 0.05% to about 2.0% by weight of the total composition. Generally, an effective amount of EDTA is from about 0.025% to about 0.5% and an effective amount of sorbic acid is generally from about 0.001% to about 0.35%, all by weight of the total composition. It is to be understood that the desired effect, maintaining sterility, can also be achieved by using higher concentrations of the foregoing compounds. Ascorbic acid, or a salt thereof, may be present in an effective amount, usually of from about 0.1% to about 20% calculated as ascobic acid. Suitable salts of ascorbic acid include the sodium and calcium salts thereof.

In accordance with another aspect of the present invention, a method is provided for maintaining the sterility of contact lens cleaning formulations which method includes providing in the formulation a preservative system in accordance with the invention. The sterility of the solution is preserved while avoiding the use of bactericides which are absorbed by soft lenses and which are incompatible with ocular tissue or otherwise cause eye irritation and/or lens discoloration.

In accordance with the preferred aspects of the present invention, a highly effective prophylactic soft contact lens cleaning composition is provided. The preferred cleaning composition is an aqueous solution that effectively removes protein, lipid and other deposits and materials that tend to adhere to the lens surfaces which are accumulated from normal lens wearing. The preferred cleaning composition according to the invention can be easily and quickly rinsed from the lens surfaces after cleaning is accomplished.

Preferably, the aqueous cleaning composition according to the invention comprises a non-ionic detergent system, a preservative system, a rinsing aid, and has a tonicity of from about 1.0 to about 2.0 and a pH of from about 6.0 to about 7.0.

In accordance with one embodiment of the invention, an aqueous cleaning composition is provided that is especially suitable for cleaning soft contact lenses. The cleaning composition contains a preservative system of the above description and a cleaning component or components. Any suitable detergent or other type of cleaning component may be utilized that is suitable for cleaning contact lenses. If the cleaning composition is intended for cleaning soft contact lenses, then the detergent or cleaning component should be suitable for use with soft contact lenses.

The surfactants which are employed generally should be completely miscible with water at the concentrations employed and generally should provide a clear solution. In addition, the surfactant must be stable under the disinfecting conditions, must not act adversely with the soft contact lens, nor with other materials present in the solution and, finally, must not irritate the eye. Therefore, the surfactant must not be adsorbed by the soft contact lens, while preferably being capable of solubilizing the proteinaceous and lipid materials adsorbed on the lens and preventing redeposition during the disinfection treatment and subsequent storage.

One group of suitable surfactants is the non-ionic surfactants, particularly hydroxyalkylated surfactants and polyoxyalkylated surfacants. Extremely effective at very low concentrations are N-hydroxyalkylated carboxamides of fatty acids of from 10–18 carbon atoms, preferably of from 12–14 carbon atoms and having from 0–1 site of olefinic unsaturation as the only unsaturation, preferably saturated. There will normally be two hydroxyalkyl groups of from 2–3 carbon atoms, which may be the same or different.

The polyoxyalkylated non-ionic detergents may be solely polyoxyalkylene groups of from 2–3 carbon atoms or may have a polyoxyalkylene chain bonded directly or indirectly to an aliphatic chain of from 10–18 carbon atoms. The alkyl containing group may be a sorbitan ester, an alkylphenyl, alkyl, a carboxylic acid, or the like. The polyoxyalkylene chain may be a homo-oligomer or co-oligomer, with the homo-oligomer normally being ethyleneoxy groups and the co-oligomer being a random or block co-oligomer of ethyleneoxy and propyleneoxy groups. These various non-ionic detergents are commercially available under a wide variety of trade names, such as Tween, Igepal, Pluronic, Brij, and Myrj. The alkylene oxy chains will generally range on the average from about 5 to 60 oxyalkylene units.

The ampholytic detergents will normally be betaines having an aliphatic carbon chain bonded to nitrogen of from about 10–18 carbon atoms, preferably from about 10-14 carbon atoms. Of particular interest are compounds of the following formula

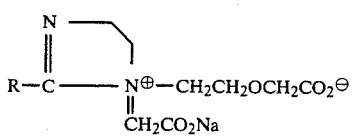

wherein R is of from 9-13 carbon atoms, usually 11 carbon atoms.

More specifically, the non-ionic cleaner may be a poly(oxyethylene)-poly(oxyethylene) block copolymer. Suitable block copolymers include those sold under the trademark "Pluronic" by the BASF-Wyandotte Chemical Corp., for example. Examples of suitable amphoteric surfactants and methods of making them are found in U.S. Pat. Nos. 2,781,349; 2,781,350; 2,781,351; 3,231,580; 3,231,581; 3,452,042; 3,658,895; and 3,697,452. Especially suitable amphoteric surfactants are available from the Miranol Chemical Company, Inc. under the trade name Miranol Amphoteric Suface Active Agents. One specific amphoteric surfactant is available as Miranol $H_2M$ concentrate.

It is to be understood that the invention is not limited to the foregoing types of cleaners, detergents or surfactants. Any type of material which can be used to clean contact lenses and which is compatible with the preservative system of the present invention and is otherwise suitable for use in a contact lens cleaning solution can be utilized, whether an aqueous solution or a gel.

Preferably, the non-ionic detergent system comprises three distinct types of non-ionic detergents. One of the non-ionic detergents is a polyoxypropylene-polyoxyethylene block copolymer having a molecular weight of from about 1,100 to about 14,000. Preferably, the polyoxyethylene or hydrophilic unit of the block copolymer is about 70% to about 80% of the total molecular weight of the block copolymer, the remainder of the block copolymer being composed of polyoxypropylene or hydrophobic unit. The block copolymer is generally present in an amount of from about 1.0% to about 15.0% by weight of the total aqueous composition. Another type of detergent in the non-ionic detergent system is an amphoteric surface active agent, generally present in an amount of from about 0.5% to about 8.0% by weight of the total aqueous composition. The preferred amphoteric surface active agent is 2-Cocoyl-2-imidazolinium lauryl sulfate-1-carboxymethyloxyethyl-1 carboxymethyl disodium. The other type of non-ionic detergent present in the detergent system of the preferred composition according to the invention is an alkylaryl polyether alcohol that is water soluble. The preferred type of alkylaryl polyether alcohol is an isoctylphenoxypolyethoxyethanol. This component is generally present in an amount of from about 0.005% to about 8.0% by weight of the total aqueous composition.

Preferably, propylene glycol is present in the cleaning compositions in accordance with the invention in an amount of from about 0.005% to about 5.0% by weight of the total aqueous composition. Propylene glycol helps provide for ease of rinsing the cleaning composition from the contact lens surface and also acts as a preservative of the composition and a thickening agent.

Compositions in accordance with the invention generally have a pH of from about 6.0 to about 7.0 and preferably from about 6.0 to about 6.5. This slightly alkaline pH helps to dissolve protein and aids in rinsing the composition from the lens. Sodium bicarbonate may be present in the composition, generally from about 0.01% to about 3.0% by weight of the total composition for adjustment of pH.

The soft contact lens cleaning compositions according to the invention preferably have a tonicity of from about 1.0 to about 2.0. Thus, the compositions of the invention can be mildly hypertonic to help prevent possible absorption into the lens matrix of foreign matter, bacteria or other residue which could build up and cause contamination problems and deterioration and discoloration of the lens itself. The remainder of the composition is purified water U.S.P.

DETAILED DESCRIPTION OF THE INVENTION

The use of appropriate antiseptic bactericidal and fungicidal chemical agents requires that the selected chemical agents be compatible with all other components of the solution as well as with the contact lens material. The essential considerations in determining the optimum antibacterial and antifungal agents are: (1) does not bind to protein; and (2) does not react with or absorb to the soft lens material or matrix. The preservative systems of the invention meet these requirements.

According to the invention, the preservative system, which provides antibacterial and antifungal activity, will usually include from about 0.05% to about 2.0% trimethoprim, preferably from about 0.075% to about 0.3% and most preferably about 0.1% by weight of the total composition. Trimethoprim is also known as 2,4-Diamino-5-(3,4,5-trimethoxybenzyl)-pyrimidine and as syraprim. See, for example, *The Merck Index*, eighth edition, pg. 1,077.

Adjuvant bactericides are also present in the preservative system, which will usually include from about 0.025% to about 0.5%, preferably 0.1%, by weight of the total composition, of ethylenediaminetetraacetic acid or a water soluble salt thereof which has bactericidal properties. The other adjuvant bactericide present is sorbic acid, usually present in an amount of from about 0.001% to about 0.35%, more desirably from about 0.01% to about 0.20%, and preferably about 0.125% by weight of the total composition. Sorbic acid is believed necessary to kill *Pseudomonas aeruginosa* bacteria, to which contact lenses and cleaning solutions are susceptible to exposure. Other types of bacteria and other organisms to which the solutions are susceptible to exposure and which are necessary to protect against are adequately rendered inactive or killed by the trimethoprim, the effectiveness of which is enhanced by the presence of EDTA and sorbic acid. While sorbic acid has antibacterial and antifungal properties, being active against molds and yeasts and to a lesser degree against bacteria, its maximum effectiveness is usually achieved at a pH of about 4.5. As the pH increases, the effectiveness of sorbic acid decreases, and at a pH of 6.5 or more, it is not particularly effective and is not suitable as a primary antibacterial agent of the compositions in accordance with the invention. However, sorbic acid has been found to act as an adjuvant bactericide for trimethoprim.

The ascorbic acid compound which may be present in the preservative system in place of or in addition to sorbic acid is present in a concentration sufficient to preserve the sterility of solutions for contact lenses when combined with the other components of the preservation system. Generally, an amount of between about 0.1% and 20% by weight of the total composition calculated as ascorbic acid is a sufficient concentration to preserve sterility. Usually, the amounts of ascorbic acid will be less than about 5% by weight of the total solution composition. The actual weight percent of the ascorbic acid salt will be that weight percent of salt required to achieve a molar concentration of the ascorbic acid ion that is equal to the molar concentration of ascorbic acid at a given weight percent. For example, if it is desired to produce a solution of an ascorbic acid salt equivalent to 10% by weight ascorbic acid, the molar concentrations "x", of a 10% by weight solution of ascorbic acid is computed. The weight percent of the ascorbic acid salt required to provide an ascorbic acid ion molar concentration of that amount, "x", is the actual weight percent of the ascorbic acid salt that is utilized. It is known that ascorbic acid is readily oxidized. Therefore, the sodium salt of ascorbic acid is preferably utilized, sodium ascorbate.

In D value studies to demonstrate the log kill of microorganisms, ascorbic acid at concentrations of 1.0% to 5.0% was shown to produce a significant log kill of 5 selected microorganisms, including *Pseudomonas aeruginosa* and *Stephylococcus aureus* within a six hour time period. Since ascorbic acid is naturally present in the human body and is nontoxic to ocular tissue in relatively large amounts, it is believed to be safe and efficacious ingredient.

When ascorbic acid is utilized, preferably monothioglycerol is included in an amount effective to stabilize the ascorbic acid compound. Most preferably, in this embodiment monothioglycerol is present in a weight ratio of monothioglycerol to the ascorbic acid compound, calculated on the basis of ascorbic acid, of 1:50. Thus, for example, if the concentration of the ascorbic acid compound is 10%, calculated on the basis of ascorbic acid, the concentration of monothioglycerol is 0.2% by weight.

When ascorbic acid is utilized in the preservative system, in order to increase the shelf life, the compositions are formulated and packaged in an atmosphere that is substantially devoid of free oxygen. For example, the compositions can be formulated and sealed in sterile containers, in the presence of a nitrogen or carbon dioxide atmosphere. Further, it is advantageous for the ascorbic acid compound to be packaged in a non-transparent container to reduce degradation that can be caused by ultraviolet radiation. The ascorbic acid could also be packaged separately, until the time of use, for example.

The preferred prophylactic cleaning compositions of the present invention also include propylene glycol. Propylene glycol is usually present in an amount of from about 0.005% to about 5.0% by weight of the total aqueous composition.

The preferred concentration of propylene glycol is about 1.0% by weight of the total aqueous composition. Propylene glycol acts as a humectant, increases the viscosity, body and feel of the cleaner without interfering with the detergent action of the detergent system. In addition, the propylene glycol also acts as a preservative and fungal growth inhibitor. Further, the propylene glycol aids in eliminating fogging of the soft contact lenses, which in itself is a major problem to soft contact lens wearers. Another important aspect of propylene glycol in the prophylactic composition of the present invention is that it permits the composition to be easily rinsed from the lens after cleaning has been accomplished.

The inclusion of ethylenediaminetetraacetic acid or a water soluble salt of ethylenediaminetetraacetic acid serves as a buffering and preservative component of the composition according to the invention, and has also been demonstrated to have antibacterial and antifungal properties. The preferred salt of ethylenediaminetetraacetic acid is disodium ethylenediaminetetraacetate (disodium EDTA or disodium edetate). Other salts of EDTA which may be utilized include, for example, mono-, di-, tri- and tetra-alkali metal salts.

The non-ionic detergent system of the composition according to the invention preferably contains three different types of non-ionic surface acting agents or detergents, each of which should be compatible with the contact lens material. The synergistic affect of the combined detergents causes both proteins and lipids to be removed from the lens surfaces when the cleaning composition according to the invention is used. The three types of non-ionic detergents preferably present in the composition of the present invention are: (1) a polyoxypropylene-polyoxyethylene block copolymer; (2) an amphoteric surface active agent; and (3) an alkylaryl polyether alcohol. Satisfactory results can also be obtained with an embodiment of the invention having the following two types of non-ionic detergents: (1) an amphoteric surface active agent; and (2) an alkylaryl polyether alcohol.

The block copolymer used in the preferred composition of the present invention are polyoxypropylene-polyoxyethylene block copolymers which are compatable with soft contact lenses. The block copolymers for use in accordance with the preferred embodiment of the invention have a molecular weight of about 1,100 to about 14,000 and a water solubility in excess of 10 grams per 100 milliliters. Preferably, about 70% to about 85% of the total molecular weight of the block copolymer consists of the hydrophilic polyoxyethylene group with the remaining weight of the molecule representing the hydrophobic polyoxypropylene base and possesses relatively low foaming characteristics.

One group of block copolymers suitable for use in the composition according to the present invention are those sold by BASF-Wyandott Corporation of Wyandott, Mich., under the trademark "Pluronic." The following Pluronic block copolymers are suitable for use in the composition of the present invention and are set forth for example and not limitation: Pluronic F-68, Pluronic F-77, Pluronic P-75, Pluronic P-65, Pluronic L-64, Pluronic F-87, Pluronic F-88, Pluronic F-98, Pluronic F-108 and Pluronic F-127. The block copolymer is generally present in the preferred composition of the present invention in an amount of from about 1.0% to about 15.0% by weight of the total aqueous composition, and preferably comprises about 6.0% by weight of the total aqueous composition. Preferably, the block copolymer used in accordance with the invention has relatively low foaming characteristics.

The preferred type of amphoteric surface active agent is 2-Cocoyl-2-imidazolinium lauryl sulfate-1-carboxymethyloxyethyl-1-carboxymethyl disodium which is also sold under the trade name "Miranol 2 MCA Modified" by the Miranol Chemical Company, Inc. of Irvington, N.J. The amphoteric surface active agent is present in the preferred composition of the present invention in an amount of from about 0.5% to about 8.0% of the total weight of the aqueous composition and preferably comprises about 3.0% of the total aqueous composition. One substitute for "Miranol 2 MCA Modified" is "Miranol MHT" which is also sold by the Miranol Chemical Company, Inc.

The third type of non-ionic detergent which may be present in the detergent system is an alkylaryl polyether alcohol. The preferred type of alkylaryl polyether alcohol in the composition of the present invention is isooctylphenoxypolyethoxyethanol. The most preferred type of isooctylphenoxypolyethoxyethanol contains about 9 units of ethoxyethanol per unit of isooctylphenol and has a molecular weight of about 630. The most preferred alkylaryl polyether alcohol is sold under the trademark "Triton X-100" by the Rohm & Haas Company of Philadelphia, Penn. The alkylaryl polyether alcohol is present in a concentration of from about 0.005% to about 5.0%, and preferably about 1.0%, by weight of the total aqueous composition. The alkylaryl polyether alcohols are also known as octylphenolethyleneoxide. The alkylaryl polyether alcohol complements the cleansing characteristics of the block copolymers and helps to remove ocular secretions, proteinaceous deposits and other materials which may be deposited upon the surfaces of the lens.

The remainder of the composition is purified water U.S.P. and preferably includes combinations of essentially neutral and alkaline salts compatible with ocular tissue and soft contact lens material which are water soluble, generally present in a concentration to provide an aqueous composition salt content equivalent to from about 1.2 to about 1.7 tonicity. Thus, the soft contact lens cleaning solutions of the present invention can be mildly hypertonic which helps in the prevention of possible absorption into the lens matrix of foreign matter, protein, lipids and bacteria which could build up and cause contamination problems and deterioration and discoloration of the lens itself. Sodium chloride can be present in the soft contact lens cleaning composition in an amount from about 0.05% to about 2.0% by weight of the total aqueous composition and preferably in an amount of about 0.748% by weight of the total aqueous composition. Potassium chloride is another salt which is preferably used in conjunction with sodium chloride and should generally be present in an amount of from about 0.05% to about 2.0% by weight of the total aqueous composition and preferably in an amount of about 0.28% by weight of the total aqueous composition.

The pH of the soft contact lens cleaning composition of the present invention is preferably slightly alkaline. The preferred pH range is from about 6.0 to about 6.5. Sodium bicarbonate can be present in the composition in an amount from about 0.01% to about 3.0% by weight of the total aqueous composition and preferably in an amount of about 0.1% by weight of the total aqueous composition.

The aqueous cleaning compositions according to the present invention are preferably utilized as part of the total patient regimen for maintaining and treating soft and semi-hard contact lenses. Thus, an effective method of contact lens storage is an important part of any effective soft or semi-hard contact lens treatment and maintenance regimen. Separate cleaning of the lenses with the preferred cleaning composition according to the present invention helps to insure that gross organic or inorganic deposits and pollutants are removed, including both proteins and lipids from the surfaces of the lenses to minimize wearing discomfort and to maximize clear vision with soft contact lenses. The preferred cleaning composition according to the present invention allows for a rapid and efficient cleaning of the lens without any need for excessive rubbing. For example, excessive rubbing between a thumb and forefinger could cause tearing or scratching of the lens which, in addition to being deleterious from a vision standpoint, could also permit the accumulation of dirt and other deposits into the scratches and/or tears. In addition, the preferred soft contact lens cleaning composition according to the present invention allows for fast and easy rinsing of the cleaning composition from the lens after cleaning has been accomplished which reduces the amount of wear and tear exerted on the lens from cleaning. Use of the composition also eliminates the need for use of an enzymatic cleaner.

Whereas the present invention has been described with respect to specific embodiments thereof, it will be understood that various changes and modifications will be suggested to one skilled in the art and it is intended that the invention encompass such changes and modifications as fall within the scope of the appended claims.

I claim:

1. A contact lens cleaning composition comprising:
   (a) trimethoprim;
   (b) a first adjuvant bactericide comprising ethylenediaminetetraacetic acid or a water soluble salt thereof and a second adjuvant bactericide selected from the group consisting of: sorbic acid; ascorbic acid; sodium ascorbate; calcium ascorbate; and mixtures thereof;
   (c) at least one cleaning component suitable for cleaning contact lenses; and
   (d) said trimethoprim and said first and second adjuvant bactericides present together in effective amounts for maintaining the sterility of the composition.

2. The cleaning composition as recited in claim 1 wherein said trimethoprim is present in an amount of from about 0.05% to about 2.0% by weight of the total cleaning composition.

3. The cleaning composition as recited in claim 1 wherein said trimethoprim is present in an amount of from about 0.075% to about 0.3% by weight of the total cleaning composition.

4. The cleaning composition as recited in claim 1 wherein said ethylenediaminetetraacetic acid or salt thereof is present in an amount of from about 0.025% to about 0.5% by weight of the total cleaning composition.

5. The cleaning composition as recited in claim 1 wherein the disodium salt of ethylenediaminetetraacetic acid is present in the composition.

6. The cleaning composition as recited in claim 1 wherein said second adjuvant bactericide is sorbic acid present in an amount of from about 0.001% to about 0.35% by weight of the total cleaning composition.

7. The cleaning composition as recited in claim 1 wherein said second adjuvant bactericide is sorbic acid present in an amount of from about 0.01% to about 0.2% by weight of the total cleaning composition.

8. A cleaning composition for cleaning contact lenses comprising:
   (a) trimethoprim;
   (b) a first adjuvant bactericide comprising ethylenediaminetetraacetic acid or a water soluble salt thereof and a second adjuvant bactericide selected from the group consisting of: sorbic acid; ascorbic acid;

sodium ascorbate; calcium ascorbate; and mixtures thereof;
(c) an alkylaryl polyether alcohol present in an amount of from about 0.005% to about 8.0% by weight of the total cleaning composition;
(d) an amphoteric surface active agent present in an amount of from about 0.5% to about 8.0% by weight of the total cleaning composition; and
(e) said trimethoprim and said first and second adjuvant bactericides present together in effective amounts for maintaining the sterility of the composition.

9. The cleaning composition as recited in claim 8 wherein:
(a) said amphoteric surface active agent is 2-Cocoyl-2-imidazolinium lauryl sulfate-1-carboxymethyloxyethyl-1-carboxymethyl disodium and is present in an amount of from about 0.5% to about 8.0% by weight of the total cleaning composition; and
(b) said alkylaryl polyether alcohol is an isooctylphenoxypolyethoxyethanol.

10. The cleaning composition as recited in claim 8 further comprising from about 0.005% to about 5.0% propylene glycol by weight of the total cleaning composition.

11. The cleaning composition as recited in claim 8 further comprising a polyoxypropylene-polyoxyethylene block copolymer having a molecular weight of from about 1,100 to about 14,000 and a water solubility in excess of about 10 grams per 100 milliliters.

12. The cleaning composition as recited in claim 11 wherein:
(a) said polyoxypropylene-polyoxyethylene block copolymer is relatively low foaming; and
(b) said amphoteric surface active agent is 2-Cocoyl-2-imidazolinium lauryl sulfate-1-carboxymethyloxyethyl-1-carboxymethyl disodium and is present in an amount of from about 0.5% to about 8.0% by weight of the total cleaning composition.

13. The cleaning composition as recited in claim 11 wherein:
(a) said polyoxypropylene-polyoxyethylene block copolymer is relatively low foaming;
(b) said amphoteric surface active agent is 2-Cocoyl-2-imidazolinium lauryl sulfate-1-carboxymethyloxyethyl-1-carboxymethyl disodium and is present in an amount of from about 0.5% to about 8.0% by weight of the total aqueous composition; and
(c) said alkylarly polyether alcohol is an isooctylphenoxypolyethoxyethanol.

14. The cleaning composition as recited in claim 8 wherein the pH of said composition is from about 6.0 to about 7.0.

15. The cleaning composition as recited in claim 8 wherein said composition has a tonicity of from about 1.0 to about 2.0.

16. The cleaning composition as recited in claim 8 wherein said trimethoprim is present in an amount of from about 0.05% to about 2.0% by weight of the total cleaning composition.

17. The cleaning composition as recited in claim 8 wherein said trimethoprim is present in an amount of from about 0.075% to about 0.3% by weight of the total cleaning composition.

18. The cleaning composition as recited in claim 8 wherein said ethylenediaminetetraacetic acid or salt thereof is present in an amount of from about 0.025% to about 0.5% by weight of the total cleaning composition.

19. The cleaning composition as recited in claim 8 wherein the disodium salt of ethylenediaminetetraacetic acid is present in the composition.

20. The cleaning composition as recited in claim 8 wherein said second adjuvant bactericide is sorbic acid present in an amount of from about 0.001% to about 0.35% by weight of the total cleaning composition.

21. The cleaning composition as recited in claim 8 wherein said second adjuvant bactericide is sorbic acid present in an amount of from about 0.01% to about 0.2% by weight of the total cleaning composition.

22. An aqueous composition for cleaning soft contact lenses which comprises:
(a) from about 0.05% to about 2.0% trimethoprim by weight of the total aqueous composition;
(b) a first adjuvant bactericide comprising from about 0.025% to about 0.5% ethylenediaminetetraacetic acid or a water soluble salt thereof by weight of the total aqueous composition and a second adjuvant bactericide selected from the group consisting of: (1) from about 0.001% to about 0.35% sorbic acid by weight of the total aqueous composition; (2) from about 0.1% to about 20% calculated as ascorbic acid by weight of the total aqueous composition of a compound selected from the group consisting of ascorbic acid, sodium ascorbate and calcium ascorbate; (3) and mixtures thereof;
(c) from about 0.005% to about 5.0% of an isooctylphenoxypolyethoxyethanol compound having from about 9 to about 10 ethoxyethanol units per isooctylphenoxy unit by weight of the total aqueous composition;
(d) a polyoxypropylene-polyoxyethylene block copolymer having a molecular weight of from about 1,100 to about 14,000 and a water solubility in excess of about 10 grams per 100 milliliters and present in an amount of from about 1.0% to about 15.0% by weight of the total aqueous composition;
(e) an amphoteric surface active agent present in an amount of from about 0.5% to about 8.0% by weight of the total aqueous composition;
(f) propylene glycol present in an amount of from 0.005% to about 5.0% by weight of the total aqueous composition;
(g) sodium chloride present in an amount of from about 0.05% to about 2.0% by weight of the total aqueous composition;
(h) potassium chloride present in an amount of from about 0.05% to about 2.0% by weight of the total aqueous composition; and
(i) sodium bicarbonate present in an amount of from about 0.01% to about 3.0% by weight of the total aqueous composition.

23. The aqueous composition as recited in claim 22 wherein:
(a) about 70% to about 85% of the total molecular weight of the block copolymer consists of the hydrophilic polyoxyethylene group with the remaining weight of the molecule being the hydrophobic polyoxypropylene base; and
(b) said amphoteric surface active agent is 2-Cocoyl-2-imidazolinium lauryl sulfate-1-carboxymethyloxyethyl-1carboxymethyl disodium.

24. The aqueous composition as recited in claim 22 wherein:
(a) said isooctylphenoxypolyethoxyethanol compound is present in an amount of about 1.0% by weight of the total aqueous composition;

(b) said polyoxypropylene-polyoxyethylene block copolymer is present in an amount of about 6.0% by weight of the total aqueous composition;

(c) said amphoteric surface active agent is present in an amount of about 3.0% by weight of the total aqueous composition;

(d) propylene glycol is present in an amount of about 1.0% by weight of the total aqueous composition;

(e) sodium chloride is present in an amount of about 0.748% by weight of the total aqueous composition;

(f) potassium chloride is present in an amount of about 0.28% by weight of the total aqueous composition; and (g) sodium bicarbonate is present in an amount of about 0.1% by weight of the total aqueous composition.

25. The aqueous composition as recited in claim 22 wherein the pH of said aqueous composition is from about 6.0 to about 7.0.

26. The aqueous composition as recited in claim 22 wherein the tonicity of said aqueous composition is from about 1.0 to about 2.0.

27. The aqueous composition as recited in claim 22 wherein said trimethoprim is present in an amount of from about 0.075% to about 0.3% by weight of the total aqueous composition.

28. The aqueous composition as recited in claim 22 wherein said trimethoprim is present in an amount of about 0.1% by weight of the total aqueous composition.

29. The aqueous composition as recited in claim 22 wherein said ethylenediaminetetraacetic acid or salt thereof is present in an amount of about 0.1% by weight of the total aqueous composition.

30. The aqueous composition system as recited in claim 22 wherein the disodium salt of the ethylenediaminetetraacetic acid is present in the composition.

31. The aqueous composition as recited in claim 22 wherein said second adjuvant bactericide is sorbic acid present in an amount of from about 0.01% to about 0.2% by weight of the total aqueous composition.

32. A method of maintaining the sterility of a contact lens cleaning composition comprising providing in the composition a preservative system for the contact lens cleaning solution comprising:

(a) trimethoprim;

(b) a first adjuvant bactericide comprising ethylenediaminetetraacetic acid or a water soluble salt thereof and a second adjuvant bactericide selected from the group consisting of: sorbic acid; ascorbic acid; sodium ascorbate; calcium ascorbate; and mixtures thereof; and (c) said trimethoprim and said first and second adjuvant bactericides present together in effective amounts for maintaining the sterility of the composition.

33. The method as recited in claim 32 wherein said trimethoprim is present in an amount of from about 0.05% to about 2.0% by weight of the total cleaning composition.

34. The method as recited in claim 32 wherein said trimethoprim is present in an amount of from about 0.075% to about 0.3% by weight of the total cleaning composition.

35. The method as recited in claim 32 wherein said ethylenediaminetetraacetic acid or salt thereof is present in an amount of from about 0.025% to about 0.5% by weight of the total cleaning composition.

36. The method as recited in claim 32 wherein the disodium salt of ethylenediaminetetraacetic acid is present in the composition.

37. The method as recited in claim 32 wherein said second adjuvant bactericide is sorbic acid present in an amount of from about 0.001% to about 0.35% by weight of the total cleaning composition.

38. The method as recited in claim 31 wherein said second adjuvant bactericide is sorbic acid present in an amount of from about 0.01% to about 0.2% by weight of the total cleaning composition.

* * * * *

UNITED STATES PATENT AND TRADEMARK OFFICE
CERTIFICATE OF CORRECTION

PATENT NO. : 4,510,065
DATED : April 9, 1985
INVENTOR(S) : Guy J. Sherman

It is certified that error appears in the above-identified patent and that said Letters Patent is hereby corrected as shown below:

Column 1, line 51, change "superificial" to --superficial--.

Column 2, line 15, change "sodiium" to --sodium--.

Column 2, lines 31 and 32, change "conposition" to --composition--.

Column 5, line 22, change "Suface" to --Surface--.

Column 8, lines 32-33, change "compatable" to --compatible--.

Column 11, line 49, change "alkylarly" to --alkylaryl--.

Signed and Sealed this

First Day of October 1985

[SEAL]

Attest:

DONALD J. QUIGG

Attesting Officer

Commissioner of Patents and Trademarks—Designate